(12) United States Patent
Sharma (10) Patent No.: US 7,515,960 B2
(45) Date of Patent: Apr. 7, 2009

(54) METHOD AND APPARATUS TO TERMINATE VENTRICULAR TACHYCARDIA VIA PACING

(75) Inventor: Vinod Sharma, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 581 days.

(21) Appl. No.: 11/097,667

(22) Filed: Mar. 31, 2005

(65) Prior Publication Data

US 2006/0224195 A1  Oct. 5, 2006

(51) Int. Cl.
*A61N 1/362* (2006.01)

(52) U.S. Cl. .................. 607/14; 607/4; 607/5; 607/15

(58) Field of Classification Search .............. 607/4, 607/9, 14, 15
See application file for complete search history.

(56) References Cited

U.S. PATENT DOCUMENTS 5,871,510 A * 2/1999 Kroll et al. .................. 607/14
6,167,308 A   12/2000 DeGroot et al.
2005/0070966 A1* 3/2005 Sharma ...................... 607/14
2006/0149325 A1* 7/2006 Zhang ........................ 607/14

OTHER PUBLICATIONS

Josephson, Mark E., "Recurrent Ventricular Tachycardia," *Clinical Cardiac Electrophysiology: Techniques and Interpretations*, 3rd ed., Lippincott Williams & Wilkins, p. 559-560 (2002).

* cited by examiner

*Primary Examiner*—Carl H Layno
*Assistant Examiner*—Eugene T Wu
(74) *Attorney, Agent, or Firm*—Michael C. Soldner (57) ABSTRACT

An implantable device for terminating ventricular tachycardia is disclosed. The device includes a processor configured to determine a first antitachycardia pulse routine of N pulses. In the routine the first N−1 pulses are separated by a first cycle length and the Nth pulse is separated by a second cycle length that is shorter than the first cycle length. The device also comprises a lead coupled to the processor. The lead comprises an electrode configured to sense a tachycardia and further configured, under control of the processor, to administer the antitachycardia pulse routine.

6 Claims, 6 Drawing Sheets

METHOD AND APPARATUS TO TERMINATE VENTRICULAR TACHYCARDIA VIA PACING

TECHNICAL FIELD OF THE INVENTION

This invention relates to the field of implantable cardioverter defibrillators and, more specifically to a method and apparatus for terminating ventricular tachycardia via pacing.

BACKGROUND OF THE INVENTION

An internal cardioverter defibrillator (ICD) is a small device that is placed within the body, typically under the skin of the chest region, to monitor the heart and to provide electrical pulses to the heart to stop irregular heartbeats (arrhythmia) when they occur. Specifically, ICDs can be used to treat ventricular tachycardia and ventricular fibrillation. Ventricular tachycardia (VT) is an arrhythmia characterized by rapid heart rhythm that arises in the ventricle. During VT, the output of the heart is decreased due to the rapid ventricular rate and the lack of properly timed or coordinated atrial contraction. VT can result in death due to the decrease in the output of the heart.

Ventricular fibrillation (VF) is an arrhythmia characterized by rapid, irregular heart rhythm that can result in "quivering" ventricles that are unable to pump blood. A victim of VF will experience a loss of pulse and may become unconscious in a matter of seconds.

Different approaches exist for treating VT and VF. Upon the sudden onset of VF, an electrical shock (or pulse) from an external defibrillator is typically the most effective way to return the victim's heart to a normal rhythm. An electrical shock is also an effective treatment for acute VT in emergency situations. In the case of a patient with chronic (long-term) cardiac disease who is at risk of arrhythmia, the preferred treatment consists of the implantation of an ICD. If the ICD detects a dangerous arrhythmia, the ICD can provide one of several treatments.

First, if the arrhythmia is a VT, the ICD can provide antitachycardia pacing (ATP). That is, a series of small electrical pulses are produced by the ICD at rates that exceed the heart rhythm for a set time. If the initial ATP fails to halt the VT, ATP can be repeated with different pacing rhythms. ICD's can also provide cardioversion if pacing fails to stop the VT or if the ICD is programmed to provide cardioversion based on detected physiological data. Cardioversion involves the delivery of a mild shock to the heart to stop the rapid heart beat. If cardioversion fails, or if VF is detected, the ICD can provide a defibrillation shock. The defibrillation shock is stronger than the cardioversion shock, but is very effective in stopping VT and VF.

For the treatment of VT, the use of a shock for cardioversion or defibrillation is extremely effective in stopping VT. However, the large electrical shocks of cardioversion and defibrillation are uncomfortable to the patient and can more rapidly deplete the energy source of the ICD. Therefore, it is preferable to stop VT through the use of ATP. However, while current ATP schemes can be used to stop VT, the process may be take several different attempts using ATP routines of different cycle length before the VT is terminated. Therefore, a method and apparatus to improve termination of ventricular tachycardia via pacing is needed.

SUMMARY OF THE INVENTION

In one embodiment of the present invention, a method for operating an internal cardioverter defibrillator is disclosed. Initially, a first antitachycardia pulse routine is delivered to cardiac tissue. The first antitachycardia pulse comprises a series of pulses spaced by a first cycle length and a final pulse spaced at a second cycle length. The second cycle length is shorter than the first cycle length. In a next step, if the first antitachycardia pulse routine fails to terminate the ventricular tachycardia additional antitachycardia pulse routines are generated. The additional antitachycardia pulse routines comprise a series of pulses spaced by a fixed cycle length and a second final pulse spaced at a final cycle length. The final cycle length decreases in each of the additional antitachycardia pulse routines until the ventricular tachycardia is terminated.

In another embodiment of the present invention, an implantable device for terminating ventricular tachycardia is disclosed. The device includes a processor configured to determine a first antitachycardia pulse routine of N–X pulses separated by a first cycle length and a second N–X+1 pulses separated by a second cycle length that is shorter than the first cycle length. The processor is further configured to generate additional antitachycardia pulse routines of N–X pulses separated by the first cycle length and the N–X+1 to Nth pulses is separated by a final cycle length selected based on a return cycle length until the ventricular tachycardia is terminated, if the first antitachycardia pulse routine failed to terminate the ventricular tachycardia. The device also comprises a lead coupled to the processor. The lead comprises an electrode configured to sense the ventricular tachycardia and is further configured, under control of the processor, to administer the antitachycardia pulse routine and the additional antitachycardia routines.

In yet another embodiment of the present invention, a method for controlling a ventricular tachycardia characterized by a ventricular tachycardia wave circulating within a ventricular tachycardia circuit at a ventricular tachycardia cycle length is disclosed. In the method , the ventricular tachycardia wave within the ventricular tachycardia circuit is entrained by delivering a plurality of evenly spaced pulses at a first cycle length that is less than the ventricular tachycardia cycle length. Next, the ventricular tachycardia wave is terminated by a last pulse at a second cycle length that is less than the first cycle length by producing an orthodromic block in an inhomogeneous region of the ventricular tachycardia circuit.

BRIEF DESCRIPTION OF THE DRAWINGS

The present invention will hereinafter be described in conjunction with the following drawing figures, wherein like numerals denote like elements, and.

DETAILED DESCRIPTION OF THE DRAWINGS

The following detailed description of the invention is merely exemplary in nature and is not intended to limit the invention or the application and uses of the invention. Furthermore, there is no intention to be bound by any expressed or implied theory presented in the preceding background of the invention or the following detailed description of the invention.

Figure 1:
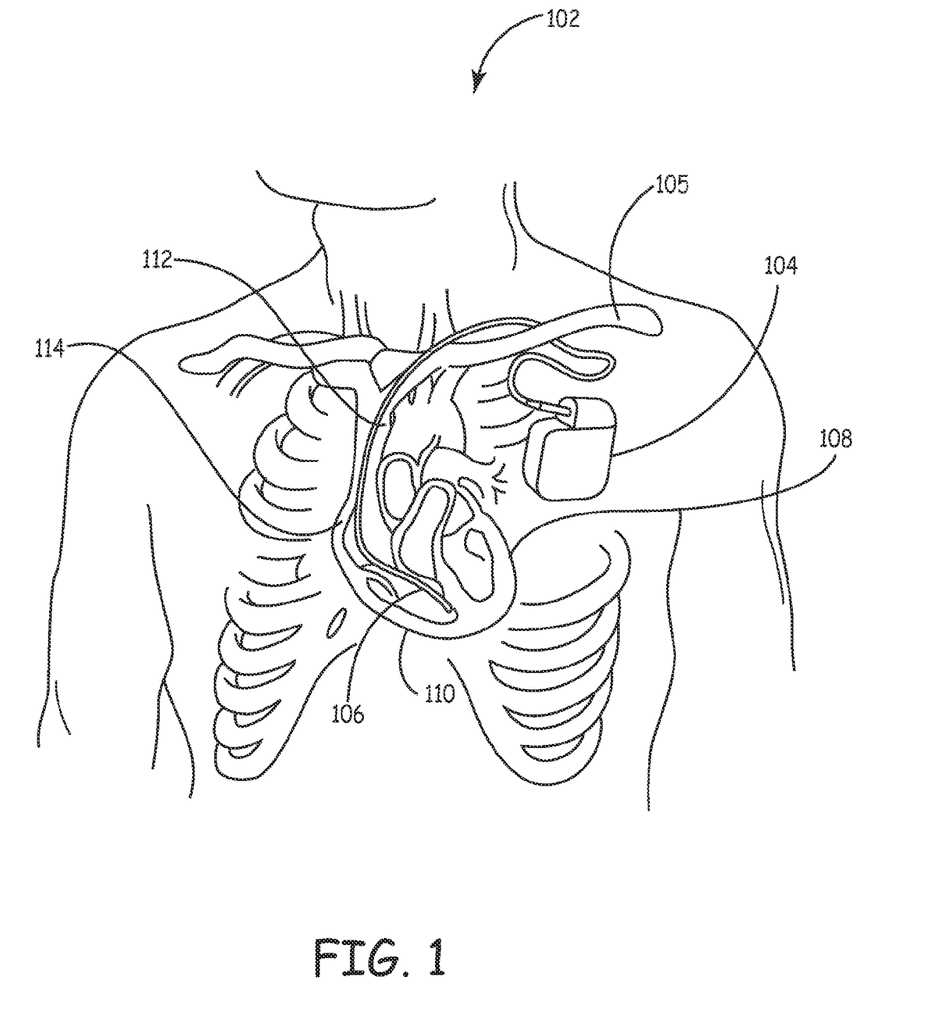
FIG. 1 illustrates an exemplary ICD placed in a patient.

FIG. 1 illustrates a patient 102 having an ICD 104 implanted therein. As seen in FIG. 1, in a typical embodiment, ICD 104 is implanted below the skin near the collarbone 105. Alternatively, the ICD 104 can be implanted in another area of the body, such as the abdomen.

The ICD 104 includes one or more leads 106 coupled to the ICD 104. The leads 106 sense the heart rhythm and send the information back to the ICD 104. The leads 106 can also conduct pulses generated by the ICD to the end of the leads 106. Typical leads 106 include two or more electrodes with one or more electrodes providing sensing capabilities and one or more providing pulse conducting capabilities. The one or more leads 106 are fed from the ICD 104 to the heart 108, through the superior vena cava 112, the right atrium 114 and into the right ventricle 110. In a typical embodiment, the lead 106 reaches to the end of the right ventricle 110.

Figure 2:
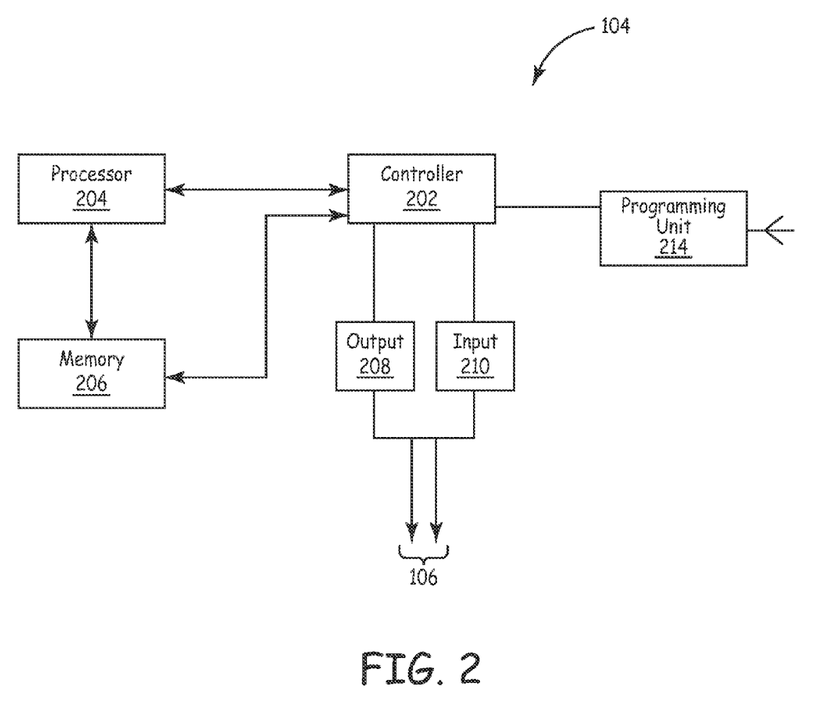
FIG. 2 is a block diagram of an exemplary ICD.

FIG. 2 is a block diagram of an illustrative embodiment of a cardioverter/pacemaker according to the present invention. As illustrated, the device is embodied as a microprocessor based stimulator. However, other digital circuitry embodiments and analog circuitry embodiments are within the scope of the invention. While the device of FIG. 2 takes the form of an ICD, the present invention may also be usefully employed in other implantable devices such as those that utilize atrial pacing and cardioversion capabilities. FIG. 2 is illustrative, rather than limiting with regard to the scope of the invention.

As seen in FIG. 2, ICD 104 comprises a microprocessor 204 coupled to a digital controller 202, that is in turn coupled to an ICD input 210, an ICD output 208, and a telemetry/programming unit 214. A memory 206 is coupled to both the microprocessor 204 and digital controller 202. In FIG. 1 lead 106 is shown as providing sensing capabilities and pulse conducting capability at the same location. However, these capabilities can be provided at different locations in the heart. For example, a detection electrode can be placed at the right ventricle and a pulse conducting electrode can be placed at the left ventricle epicardium. Memory 206 may comprise random access memory, read only memory, or a combination of random access memory and read only memory. Memory 206 can store the basic programming for the ICD 104 and can also serve to store variable control parameters, such as programmed pacing rate, programmed cardioversion intervals, pulse widths, pulse amplitudes, and so forth which are programmed into the device by the physician.

Microprocessor 204 is configured to perform any required mathematical calculations, including all operations associated with the selection of therapies according to the present invention. For example, microprocessor 204 can determine whether a tachyarrhythmia or fibrillation is present and whether to start an ATP routine, a cardioversion or a defibrillation pulse. If an ATP routine is chosen, microprocessor 204 can determine the intervals separating individual tachyarrhythmia beats, based on data collected by the ICD 104.

Controller 202 performs all the basic control and timing functions of the ICD 104. When a pacing pulse is needed or in response to a determination that a cardioversion or defibrillation pulse is to be delivered, controller 202 can trigger the appropriate output pulse from output 208, as discussed below.

ICD output 208 includes a high output pulse generator capable of generating cardioversion pulses that are to be applied to the patient's heart via lead 106. This high output pulse can be used for defibrillation or cardioversion. Typically, the high output pulse generator includes a high voltage capacitor, a charging circuit, and a set of switches to allow delivery of monophasic or biphasic cardioversion or defibrillation pulses to the electrodes employed. ICD output 208 may also include a pacing pulse generator circuit to accomplish ventricular cardiac pacing by delivery of pulses at the electrodes. ICD output 208 is controlled by controller 202, which determines the time, amplitude, and pulse width of the pulse to be delivered.

Sensing of ventricular depolarizations is accomplished by ICD input 210, which is coupled to lead 106. Signals indicating both the occurrence of natural ventricular contractions and paced ventricular contractions are provided to controller 202. Controller 202 passes data indicative of the occurrence of such ventricular contractions to microprocessor 204, which performs any necessary calculations or updating of values stored in memory 206.

Telemetry/programming unit 214 provides communication between ICD 104 and an external programmer. Any conventional programming/telemetry circuitry can be used in the present invention. Information entering the ICD 104 from the telemetry/programming unit 214 is passed to controller 202. Similarly, information from the ICD 104 can be provided to the telemetry/programming unit 214 from the controller 202.

As discussed previously, a treatment for a patient equipped with an ICD and undergoing VT is to provide a low voltage shock to the heart at a rate that is faster than the VF heart rate. This is known as antitachycardia pacing (ATP). For example, if the VT rate is 150 beats per minute, the VT cycle length (VTCL) is 400 ms (that is, there is 400 ms between each beat). The antitachycardia pacing cycle length (ATP CL) rate is set at a cycle length shorter than the VTCL. In one embodiment, the ATP CL may be set at 70% to 80% of the VTCL. Then, pulses are delivered using that cycle length for a set number of pulses. Any number of pulses can be utilized; however, the number of pulses is typically set between 4 and 24 pulses. After the pulses are delivered, the ICD 104 can determine if the VT has terminated. If not, the same ATP routine could be tried again, a new ATP routine with a shorter cycle length and/or different number of pulses may be tried or a cardioversion/defibrillation pulse could be delivered. In general, it is better for both the patient and for the longevity of the ICD 104 that ATP be used over the defibrillation or cardioversion.

Figure 3:
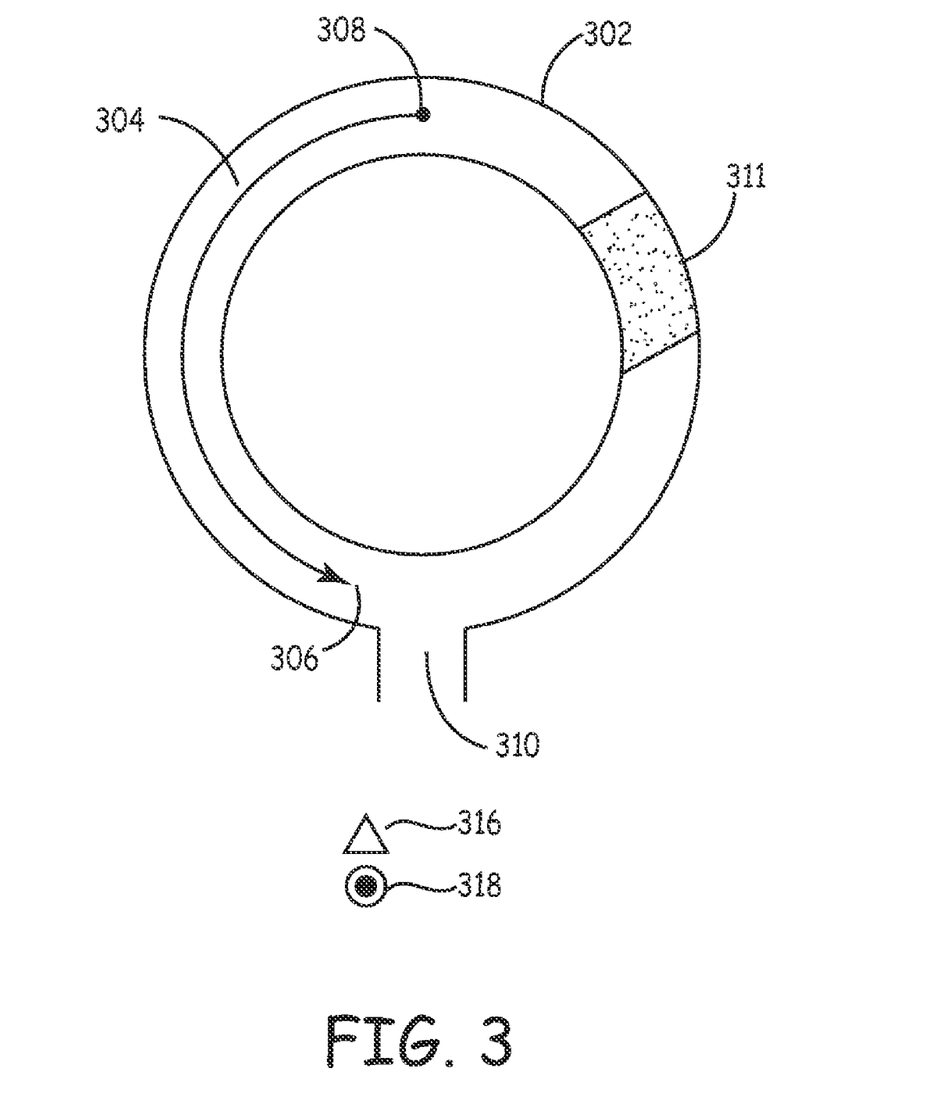
FIG. 3 is a model illustrating how VT occurs.

In typical cases of VT, the arrhythmia can result from the abnormal excitation of heart tissue resulting in an impulse that tracks around a closed circuit described below as an annular region to simplify description of ATP-VT interaction. The ATP routine attempts to terminate the VT by the introduction of a number of spaced electrical impulses sent at a rate faster than the VTCL. In theory, the pulses enter the annular region and attempt to annihilate the VT. FIG. 3 illustrates an exemplary annular region and VT wave. In FIG. 3, VT circuit 302 has a VT wave 304 traveling through at a certain circuit length. VT circuit 302 has at least one entry/exit 310. In some VT circuits 302, the entry and exit can be spaced apart from each other. Additionally, VT circuit 302 typically includes at least one inhomogeneous region 311, which represents an area where the VT wave 304 propagates at a slow velocity from the rest of the VT circuit 302. This region is also commonly referred to as a critical isthmus region. In addition, the electrophysiological properties of this inhomogeneous/critical isthmus region are such that the refractoriness of the underlying tissue is extended compared to that of the normal regions of the VT circuit 302. Refractoriness is a measure of the time it takes for excited cardiac tissue to be able to be re-excited. Inhomogeneous region 311 can be an area of damaged or diseased cardiac tissue.

A detection/pacing site can both sense an arrhythmia and emit a pacing pulse 316. The pacing pulse is one of the pulses in the ATP routine. The pacing pulse 316 released from the detection/pacing site 318 can enter the entry 310 and split into a wave traveling in two directions. One part of the pacing pulse 316 travels in the same direction as the VT wave 304 (orthodromic direction) and one in the opposite direction (antidromic direction). The pacing pulse 316 traveling in the antidromic direction can interact with a head 306 of the VT wave 304, and the pacing pulse 316 traveling in the orthodromic direction can interact with a tail 308 of the VT wave 304. In the antidromic direction the pacing pulse collides with the head 306 of the VT wave 304 and the two waves annihilate each other. The circuitous activity and the VT is annihilated in the orthodromic direction as well provided the pacing pulse 316 is able to catch up with the refractory tail 308 of the VT wave 304. Such interaction between the pacing pulse 316 and the VT wave 304 occurs in the inhomogeneous region 311, which represents damaged cardiac tissue.

However, if the pacing pulse 316 traveling in the orthodromic region fails to interact with the tail 308 of the VT wave 304 when it is in the refractory state, the VT wave 304 most likely will not be terminated but can instead be reset or entrained by the pacing pulse 316. A VT is said to be reset if a single pulse enters the VT circuit 302 and advances the VT such that the sensed beats occur sooner than the scenarios in which the pacing pulse had not entered the VT circuit 302. A VT is entrained if multiple pulses entered the VT circuit 302 wherein the first pulse advances the VT in the circuit, and each subsequent pulse then interacts with this advanced VT. Furthermore, the state of the VT within the circuit at the time of interaction with three subsequent pulses is exactly the same for all pulses.

Several factors are known to influence the ability of an ATP routine to interact with the VT wave 304. The first factor is the VTCL, which depends on the size of the VT circuit 302 and the velocity of the VT wave 304 in the VT circuit 302. The second factor is the refractory period at the detection/pacing site 318 and in the VT circuit 302. The refractory period is the time following excitation of the cardiac tissue during which the cardiac tissue cannot be excited. The third factor is the time it takes one of the pacing pulses 316 from the detection/pacing site 318 to reach the VT circuit 302. The fourth factor is the size (duration) of the excitable gap in the VT circuit 302. The excitable gap is the region of excitable tissue between the head 306 and the tail 308 of the VT wave 304. In prior art ATP routines, the initial pacing impulses are thought to "peel back" refractoriness which will allow subsequent pulses to enter the circuit earlier. However, prior art ATP routines relied on a series of evenly spaced pulses (perhaps followed by one or more other series of evenly spaced pulses) without consideration of what type of pulse rate and pattern would best work to stop VT.

In one embodiment of the present invention, a novel ATP routine is presented. The exemplary ATP routine in the present invention comprises a series of N−1 evenly spaced pulses (with the cycle length of each of these pulses set at some percentage of the VTCL). A final pulse, the Nth pulse, is delivered at a cycle length shorter than that of the N−1 previous pulses.

FIGS. 4-15 illustrate an exemplary embodiment of the present invention. In the example of FIGS. 4-15, initially the VTCL is six time units and the excitable gap is two time units. The distance between the entry/exit 310 of VT circuit 302 and the detection/pacing site 318 is one time unit and the ATP cycle length is initially set at five time units. Each time unit represents some amount of time. For example, in an exemplary embodiment each time unit could be equal to 100 ms of time.

Figure 4:
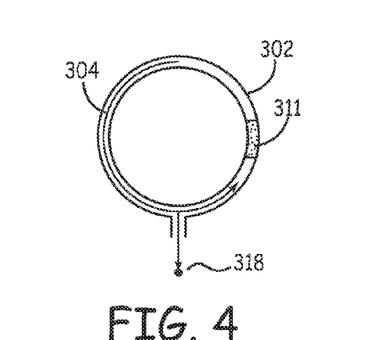
FIGS. 4-15 are illustrations of the effect of an exemplary embodiment of the present invention on ventricular tachycardia.

In FIG. 4, the VT wave 304 is traveling in the VT circuit 302 and is detected at the detection/pacing site 318. The detection of VT is confirmed after a set number of VT waves (e.g. 8 to 24) are detected at detection/pacing site 318. In FIG. 4, the VT detection occurs at zero time units. When the detection of VT is confirmed, the ATP routine is initiated. Although FIGS. 4-15 show an embodiment in which the pacing and detection functions occur at the same location, in practice the pacing and detection may be accomplished by two distinct electrodes located in two different regions of the heart. As discussed previously, a detection electrode can be located at the right ventricle apex and a pacing electrode at the left ventricle epicardium. In the latter case, a suitable time delay may be incorporated to account for the distance between the detection electrode and the pacing electrode and for adjusting the timing of the ATP pulses.

Figure 5:
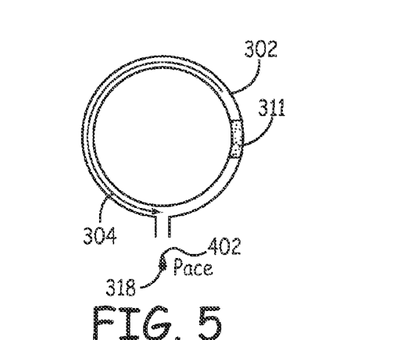

FIG. 5 illustrates the VT circuit 302 five time units later. In the five time units, the VT wave 304 has traveled not quite all the way around the VT circuit 302. Also, an initial pulse 402 has been initiated at the detection/pacing site 318. The initial pulse is the first pulse in the ATP routine.

Figure 6:
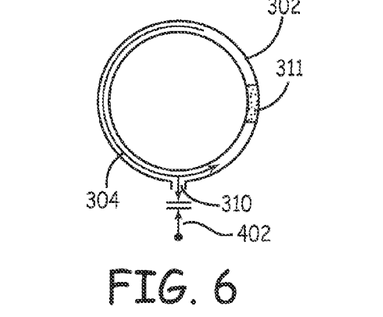

Since the distance from the detection/pacing site 318 to the VT circuit 302 is one time unit, half a time unit after the state of FIG. 5 the initial pulse 402 would travel halfway towards the VT circuit 302. This is seen in FIG. 6. Also illustrated in FIG. 6 is the VT wave 304. The VT wave 304 has also moved half a time unit and has split at the entry/exit 310. Part of the VT wave 304 continues along the VT circuit 302, and part of the VT wave 304 exits the VT circuit 302 and collides with the initial ATP pulse 402.

Figure 7:
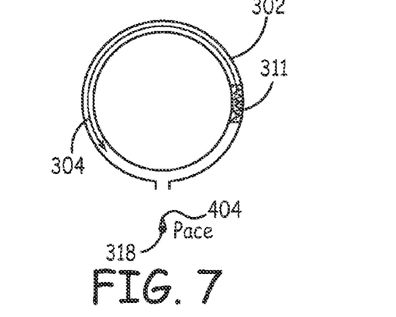

Referring to FIG. 7, a second pulse 404 is initiated at ten time units. Comparing the state of VT circuit 302 in FIG. 7 with FIG. 5, it can be seen that the VT wave 304 has been shifted backwards in the VT circuit 302 by a unit. Note, that in FIG. 7, part of the VT wave 304 is in the inhomogeneous region 311. In this region, it takes longer for the VT wave 304 to propagate and for tissue to recover so that it can support the propagation of a next VT wave. The time required by the heart tissue to recover from an excitation pulse and before it can be excited again is known as the period of refractorness. In the inhomogeneous region 311 of the VT circuit 302, the period of refractorness is longer than in the other portions of the VT circuit 302.

Figure 8:
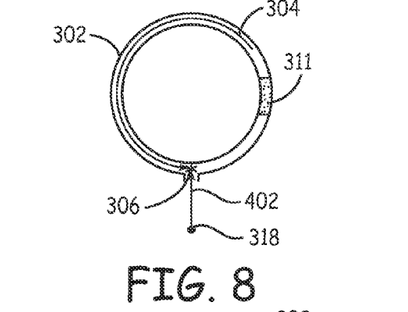

Next, as illustrated in FIG. 8, one unit after the state of FIG. 7, the second pulse 404 has reached the entry/exit point 310 of the VT circuit 302. The VT wave 304 has moved forward by one time unit. The second pulse 404 and the VT wave 304 collide at the entry 310 of the VT circuit 302. This terminates the original VT wave 304 and the VT wave 304 in the VT circuit 302 is now the result of the second pacing pulse 404. From FIG. 4 to FIG. 8, the VT wave 304 can be seen to be moving at its original pre-ATP rate within the VT circuit, although the first two ATP pulses have gradually peeled back refractoriness to reach the VT circuit. In general, the amount of refractoriness peeled away by each pulse is (VTCL-ATP CL)/2.

Figure 9:
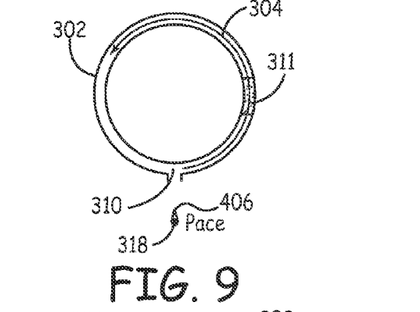
Figure 10:
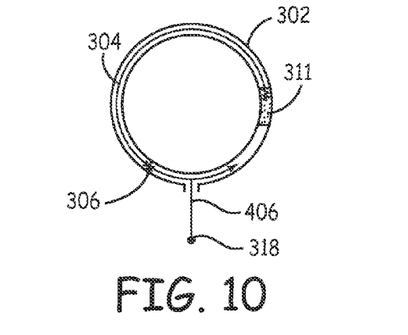
Figure 11:
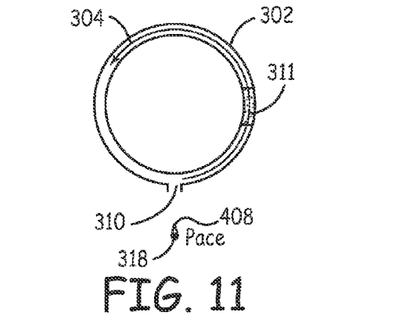
Figure 12:
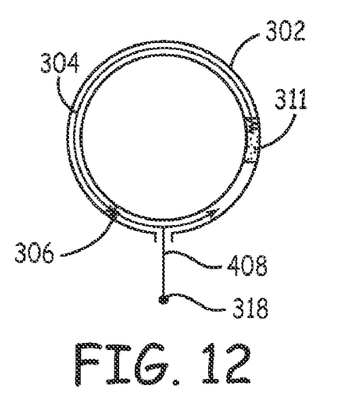

A third pulse 406 is initiated after the elapse of fifteen time units, as illustrated in FIG. 9. The VT wave 304 is shifted backwards by one time unit as compared to the state in FIG. 7, where the second pulse 404 was initiated. Then, as illustrated in FIG. 10, one and a half time units later, the third pulse 406 has moved from the detection/pacing site 318 to the entry 310 of the VT circuit 302 (which takes one time unit) and then third pulse 406 splits as it enters the VT circuit 302, with part of the third pulse 406 traveling in the orthodromic direction and part of the pulse traveling in the antidromic direction. The part of the third pulse 406 traveling in the antidromic direction collides with the VT wave 304 (i.e. the previously paced wave). The third pulse 406 traveling in the orthodromic region does not reach the tail 308 of the VT wave 304 and doe not cause any annihilation. Instead it becomes the head 306 of the new VT wave 304. At this point, the VT wave 304 is said to be entrained and any subsequent pulses sent at the same cycle length will produce the same results. For example, as seen in FIG. 11, a fourth pulse 408 initiated after twenty units of time produces an interaction that is identical to FIG. 9. FIG. 12 represents a state one and a half time units after the state shown in FIG. 11 and is the same as FIG. 10.

Figure 13:
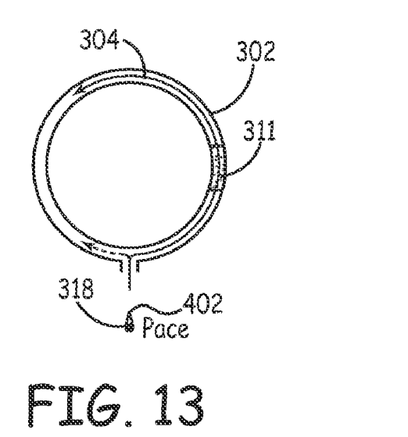

FIG. 13 illustrates the initiation of a pulse 410. This is the last pulse 410 in the ATP train and is sent at a different interval than the first four pulses. In the example of FIG. 13, the pulse is initiated at 4.5 time units after the last pulse instead of five time units.

Figure 14:
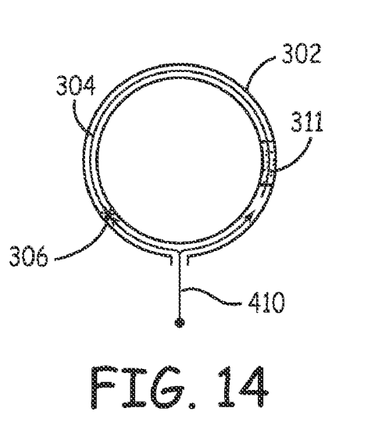

FIG. 14 illustrates the last pulse 410 of FIG. 13 one and three fourth time units after FIG. 13. The first part of the pulse 410 in the antidromic direction collides with the VT wave 304, which itself is the result of a previous paced pulse. Note that in FIG. 14, the distance between the front of the new VT wave 304 and the tail (the excitable gap) has decreased.

Figure 15:
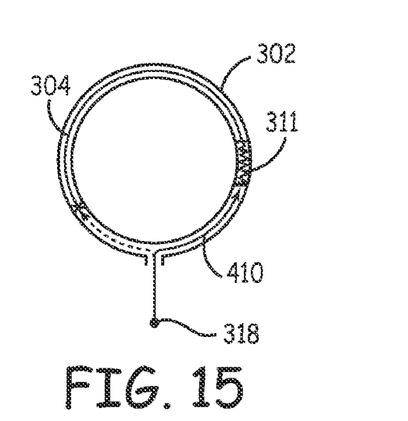

FIG. 15 illustrates the state of the VT circuit 302 half a unit of time after the state in FIG. 14. The pulse in the orthodromic path has caught up with the VT wave 304 in the inhomogeneous region 311. The final pulse 410 can catch up with the VT wave 304 because the VT wave 304 slows down in the inhomogeneous region 311. Furthermore, the head of the last pacing pulse can interact with the tail of the VT wave 304 because the refractoriness of the tissue in the inhomogeneous region 311 is longer. This allows orthodromic block in pulse propagation and VT termination.

As seen from the above discussion, an ATP routine that uses evenly spaced pulses which is more aggressive than the VT (i.e. ATP CL>VTCL) will eventually enter the circuit and extinguish the original VT, resulting in either the resetting of the VT or entrainment of the VT.

In order to achieve VT termination, an orthodromic block (interaction between a pulse and the tail of the VT wave 304 in the inhomogeneous region) needs to occur. The orthodromic block can occur, in one embodiment, when the orthodromic part of the pulse catches up to the VT wave 304 and there is a sufficient prolongation of refractoriness in the inhomogeneous region 311. The actual amount of extension in refractoriness necessary for achieving an orthodromic block can be expressed as $\Delta ERP_c > CL_n - ERP_p$; where $CL_n$ is the cycle length of the last pulse in the ATP routine, and $ERP_p$ is the effective refractory period of the paced wave fronts.

The above new ATP routine is an open loop routine; that is, the cycle for the last pulse is chosen without knowledge of how the overall system is reacting. In another embodiment of the present invention, a closed loop routine can be used. In a closed loop routine, parameters of the VT circuit 302 are examined and the cycle length of the last pulse is decremented based on the parameter examined. One particular parameter of the VT circuit 302 that can be examined is the return cycle length. The return cycle length (RCL) of a VT circuit is the time it takes to sense a VT wave 304 after the last pulse of an ATP routine, which has successfully entrained the VT, is sent from the detection/pacing site 318. For example, in FIG. 10, the RCL is eight because the circuit has been entrained (FIG. 8 onwards), and because it takes one time unit to go from the detection/pacing site 318 to the VT circuit 302, six time units to go around the VT circuit 302 and another one time unit to return to the pacing site where it can be sensed. If the RCL is increasing in the VT circuit 302, the tail 308 of the VT wave 304 is being acted upon by the head of the pulse in the critical region (the inhomogeneous region 311). Thus, if the change of the RCL is large, the VT wave should be close to termination and the adjustment to the cycle length of the final pulse can be small. However, if the change in the RCL is small, VT termination is not as imminent and a larger change in the cycle length of the final pulse can be made to more rapidly achieve ventricular tachycardia termination. A threshold value can be chosen above which a change in the RCL can be considered large and below which the change in the RCL can be considered small. The selection of the threshold can vary based on factors specific to each ventricular tachycardia.

Figure 16:
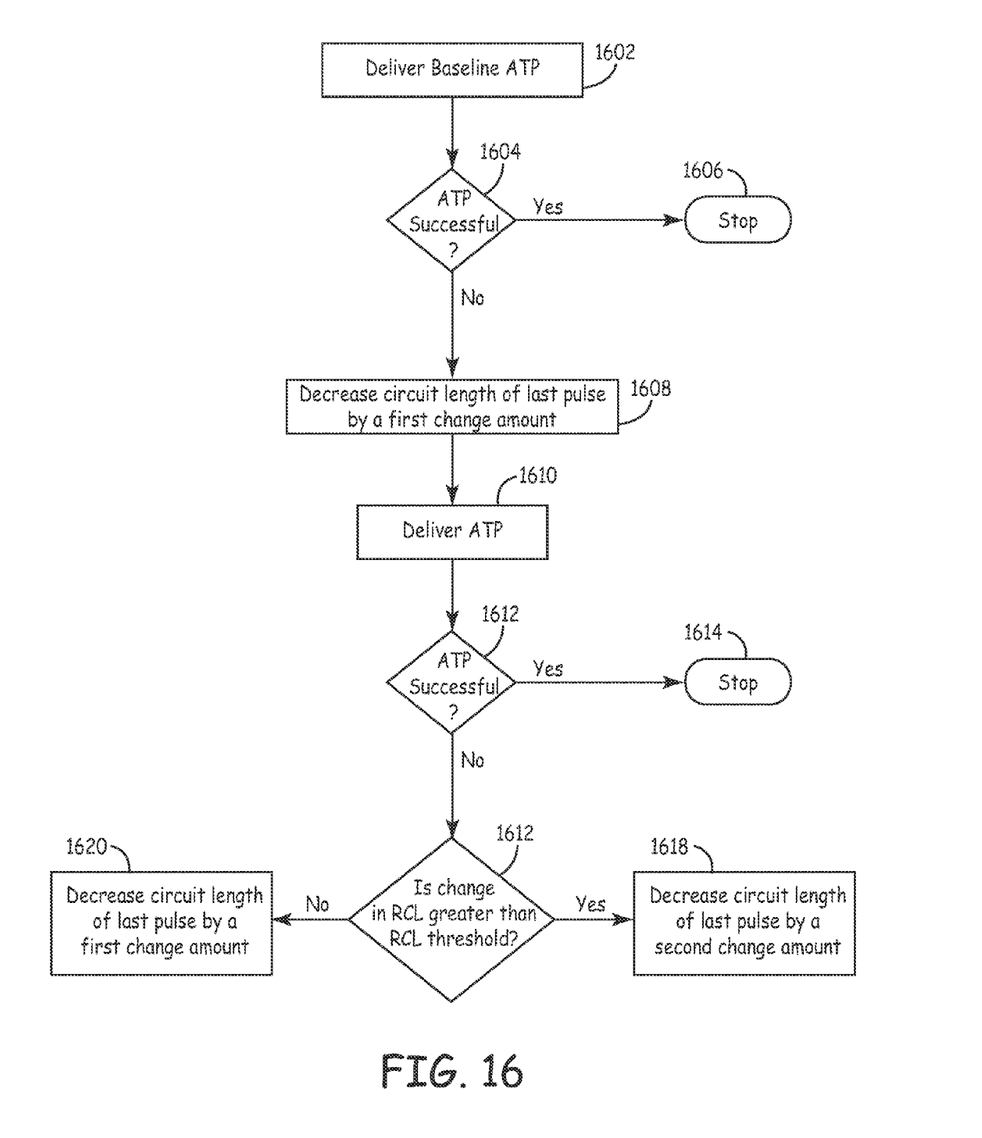
FIG. 16 is a flowchart of an exemplary embodiment of a novel ATP routine.

FIG. 16 is a flowchart illustrating a closed loop method for adjusting the last pulse 410 of an ATP routine. In a first step 1602, an initial ATP routine is delivered. The initial ATP routine can include a number of pulses spaced at some cycle length and a final pulse spaced at a shorter cycle length. In step 1604, it is determined if the initial ATP routine was successful. In step 1606, if the initial ATP routine was successful, the method ends. In step 1608, if the initial ATP failed to terminate the VT, the cycle length of the last pulse for the next ATP is decreased by a first change in cycle length. The first change in cycle length is typically a predetermined value and represents an amount of time by which the cycle length of the first pulses will be decreased to determine the cycle length of the last pulse. The first change in cycle length can be chosen based on some determination of how much change in the last pulse cycle length is desired. Since initially it has not yet been determined if an aggressive change in cycle length for the last pulse is needed, the first change selected in cycle length may be chosen to be a smaller, less aggressive change.

In step 1610, the second ATP is delivered. The second ATP routine can be the same as the first except that the change in cycle length for the last pulse has been decreased by the first change in cycle length. If the VT has been terminated (step 1612), the method ends at step 1614.

If the VT was not terminated, a change in the return cycle length is determined in step 1616. This is determined by determining the current RCL and comparing it to the RCL of a previous ATP train. Next, it is determined if the change in the RCL is larger or smaller than a predetermined threshold in step 1618. If the change in RCL is larger than the threshold, this indicates a lengthening of the RCL and that the head of the pulse is close to the tail of the VT wave. Thus, only a small change in the cycle length of the last pulse is needed. Therefore, in one embodiment, the cycle length of the last pulse is decreased by the first change in cycle length in step 1620 and the method continues in step 1610.

If the change in RCL is smaller than the threshold, a more aggressive change in cycle length can be chosen in order to more quickly move towards a pulse that will stop VT. Therefore, in step 1622, the second change in cycle length for the last pulse is subtracted from the current cycle length and is chosen to be greater than the first change in cycle length. The method then continues in step 1610.

While an exemplary embodiment has been presented when the last pulse is sent at a shorter cycle length that the other pulses in an ATP routine, the last pulse can be more than one pulse delivered at a cycle length shorter than the ATP CL. That is, a final pulse may represent one or more final pulses. For example, given an ATP routine of N pulses, there can be X final pulses and N–X initial pulses where X is one or more. The cycle length of each successive X final pulses can change.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed:

1. A method for operating an internal cardioverter defibrillator to terminate ventricular tachycardia, the method comprising:

generating a first antitachycardia pulse routine comprising a series of pulses spaced by a first cycle length and a first final pulse spaced at a second cycle length, the second cycle length shorter than the first cycle length;

if the first antitachycardia pulse routine fails to terminate the ventricular tachycardia, generating additional antitachycardia routines comprising a second series of pulses spaced by the first cycle length and a second final pulse spaced at a final cycle length, the final cycle length decreasing in successive antitachycardia routines until the ventricular tachycardia is terminated: and determining the final cycle length of the second final pulse based on a return cycle length of the ventricular tachycardia wave.

2. The method of claim 1, wherein determining final cycle length of the second final pulse further comprises:

comparing a current return cycle length against a previous return cycle length;

decreasing the final cycle length by a first amount if the current return cycle length exceeds the previous return cycle length by a predetermined threshold; and decreasing the final cycle length by a second amount if the current return cycle length does not exceed the previous return cycle length by the predetermined threshold, the second amount greater than the first amount.

3. The method of claim 1 wherein generating a first antitachycardia pulse routine comprising a first series of pulses further comprises generating the first antitachycardia pulse routine with the first final pulse comprising two or more pulses spaced apart by a cycle length shorter than the first cycle length.

4. The method of claim 1, wherein generating additional antitachycardia pulse routines further comprises generating the additional antitachycardia pulse routines with the second final pulse comprising two or more pulses spaced apart by a cycle length shorter than the first cycle length.

5. The method of claim 1 further comprising:

sensing physiological data at a first location in a patient's heart; and delivering the first antitachycardia pulse routine at a second location in the patient's heart, the first location and the second location spaced apart.

6. The method of claim 5 further comprising:

analyzing the physiological data from the patient; and delivering a defibrillating pulse if the physiological data indicates the patient is undergoing ventricular fibrillation.

* * * * *